US009724037B2

(12) United States Patent
Chang

(10) Patent No.: US 9,724,037 B2
(45) Date of Patent: Aug. 8, 2017

(54) WEARABLE DEVICE CAPABLE OF MONITORING PERSPIRATION

(71) Applicant: HON HAI PRECISION INDUSTRY CO., LTD., New Taipei (TW)

(72) Inventor: Jen-Tsorng Chang, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 231 days.

(21) Appl. No.: 14/754,980

(22) Filed: Jun. 30, 2015

(65) Prior Publication Data

US 2016/0058360 A1   Mar. 3, 2016

(30) Foreign Application Priority Data

Sep. 2, 2014   (CN) .......................... 2014 1 0442094

(51) Int. Cl.
 *A61B 5/00* (2006.01)
 *A61B 5/053* (2006.01)
(52) U.S. Cl.
 CPC .......... *A61B 5/4266* (2013.01); *A61B 5/0537* (2013.01); *A61B 5/6824* (2013.01); *A61B 2562/125* (2013.01)

(58) Field of Classification Search
 CPC .................................................. A61B 5/4266
 See application file for complete search history.

(56) References Cited

U.S. PATENT DOCUMENTS

2007/0017824 A1*   1/2007   Rippeth ............. G01N 27/3272
                                                              205/792

\* cited by examiner

*Primary Examiner* — Christian Jang
(74) *Attorney, Agent, or Firm* — Steven Reiss

(57) ABSTRACT

A wearable device includes a main body, a support portion, an electrode assembly, and a processor. The main body can be worn by a user. The support portion is secured to the main body and faces the user. The electrode assembly is secured to the support portion, and includes two electrode arrays and a plurality of carbon nanotubes arranged in arrays. Each electrode array includes arranged electrodes electrically connected to each other. The electrodes of each electrode array include at least two first electrodes each electrically connected to one carbon nanotube. The carbon nanotubes electrically connected to the two electrode arrays are alternatively arranged on the support portion and spaced from each other to form a detecting surface. The processor detects a resistance value of each electrode assembly, and determines an amount of the perspiration corresponding to the detected resistance value.

15 Claims, 6 Drawing Sheets

US 9,724,037 B2

WEARABLE DEVICE CAPABLE OF MONITORING PERSPIRATION

FIELD

The subject matter herein generally relates to wearable devices, and particularly, to a wearable device capable of monitoring perspiration.

BACKGROUND

As electronic devices have been made smaller, a new class of wearable devices has become popular. A wearable device can be configured to be worn by a user. The wearable device can come in the form of a watch or bracelet. Additionally, since an amount of perspiration is a critical parameter for evaluating a state of health of the user, a wearable device capable of timely monitoring of the amount of perspiration is required.

BRIEF DESCRIPTION OF THE DRAWINGS

Implementations of the present technology will now be described, by way of example only, with reference to the attached figures.

DETAILED DESCRIPTION

Figure 1:
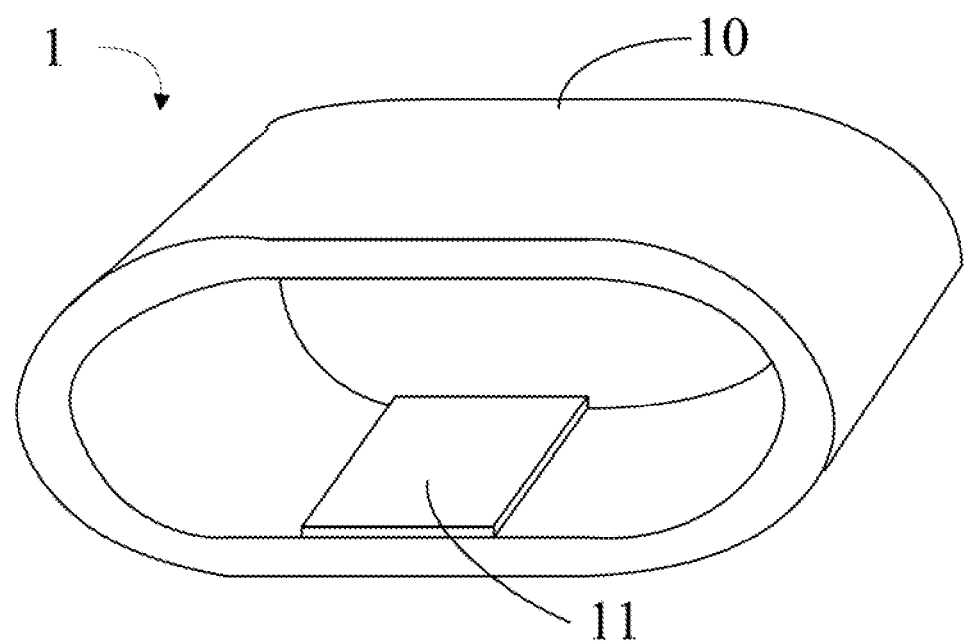
FIG. 1 is a diagrammatic view of an embodiment of a wearable device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout this disclosure will now be presented.

The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

FIG. 1 illustrates one embodiment of a wearable device 1 capable of monitoring perspiration from a user. The wearable device 1 includes a main body 10 to be worn by the user. In at least one embodiment, the main body 10 is a wristband. In another embodiment, the main body 10 is an ankle band. A support portion 11 protrudes from an interior surface of the main body 10 facing the user. The support portion 11 is made of glass or plastic. The plastic can be polyethylene terephthalate (PET) or polycarbonate (PC).

Figure 2:
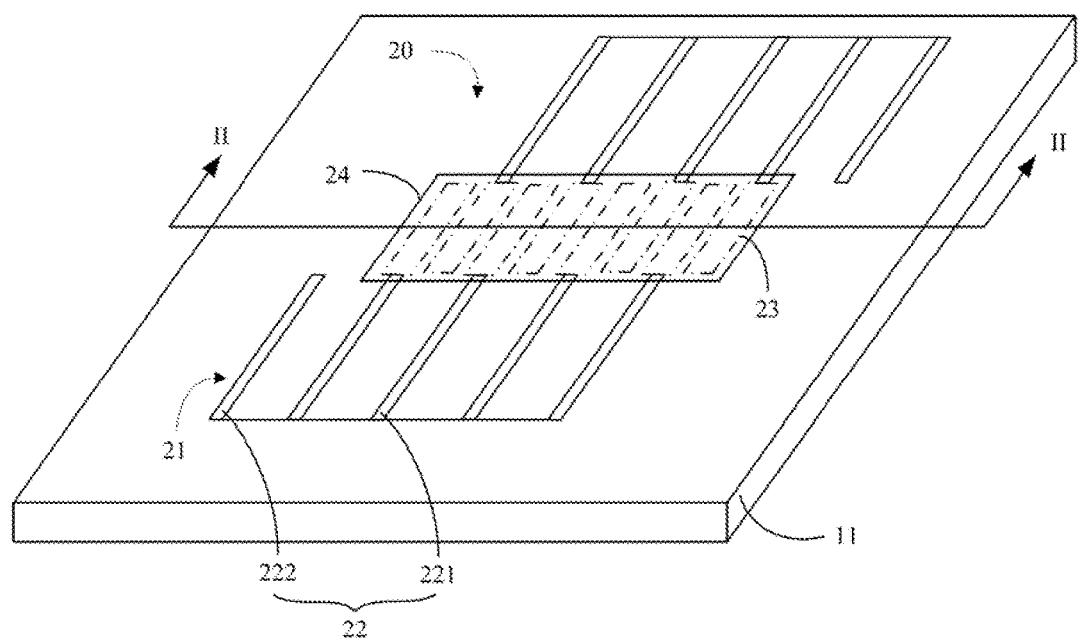
FIG. 2 is a diagrammatic view of an electrode assembly included in the wearable device of FIG. 1.

FIG. 2 illustrates that at least one electrode assembly 20 is positioned on and secured to the support portion 11. Each electrode assembly 20 includes two electrode arrays 21 and a number of carbon nanotubes 23 arranged in arrays. Each electrode array 21 includes a number of arranged electrodes 22 electrically connected to each other. In at least one embodiment, the electrodes 22 of each electrode array 21 are spaced from each other. The electrodes 22 of each electrode array 21 include at least two first electrodes 221 each electrically connected to one of the carbon nanotubes 23. In at least one embodiment, the first electrodes 221 can be connected to one of the carbon nanotubes 23 by a conductive silver adhesive (not shown). The electrodes 22 of each electrode array 21 can further include one second electrode 222 electrically disconnected from each carbon nanotube 23. The carbon nanotubes 23 electrically connected to the two electrode arrays 21 are alternatively arranged on the support portion 11 and are spaced from each other to form a detecting surface 230.

In at least one embodiment, the two electrode arrays 21 of each electrode assembly 20 face each other and are spaced from each other. The carbon nanotubes 23 are substantially parallel to each other and located between the two electrode arrays 21. An extension direction of each electrode 22 of the two electrode arrays 21 is parallel to an exial direction of the carbon nanotubes 23.

Figure 3:
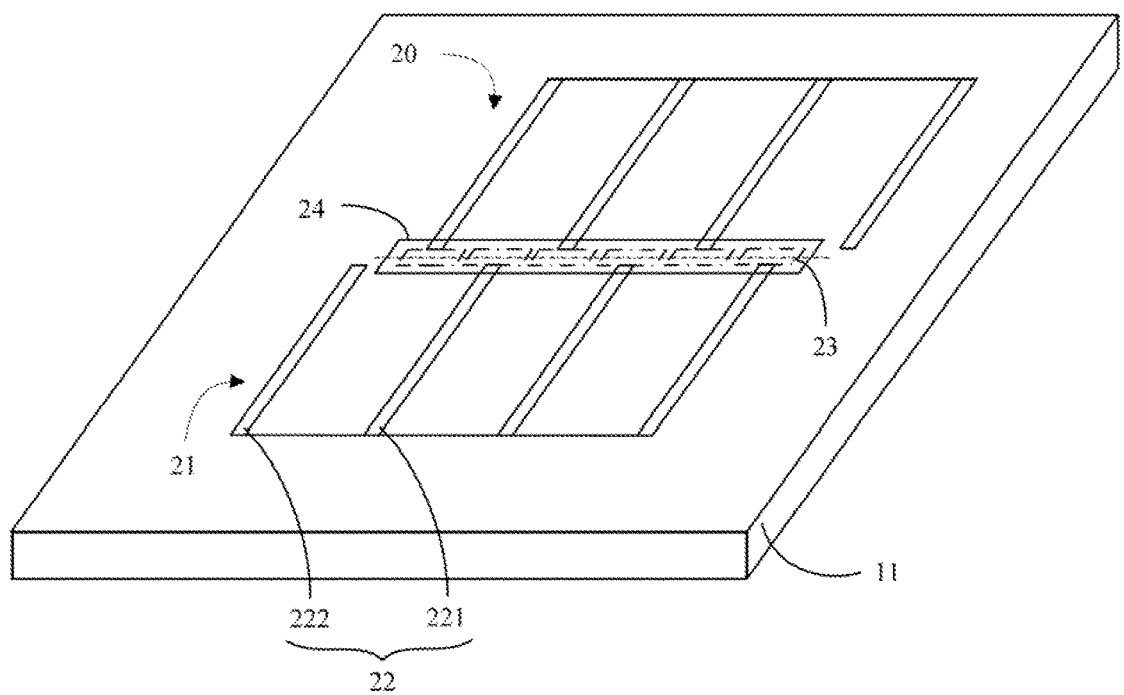
FIG. 3 is similar to FIG. 2, but showing the electrode assembly in another embodiment.

In another embodiment, the location of the two electrode arrays 21 with respect to the carbon nanotubes 23 can be varied. FIG. 3 illustrates that the extension direction of each electrode 22 of the two electrode arrays 21 can also be perpendicular to the axial direction of the carbon nanotubes 23.

Figure 4:
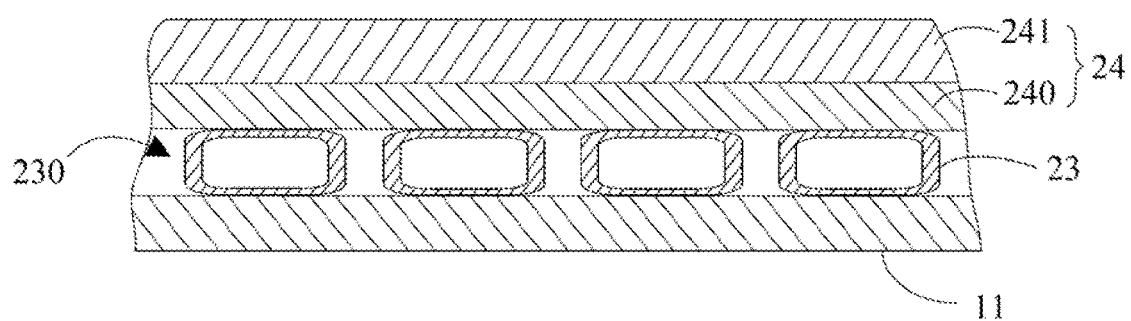
FIG. 4 is cross-sectional view taken along line II-II of FIG. 2.

FIG. 4 illustrates that a protective layer 24 is covered on the detecting surface 230. The protective layer 24 secures the carbon nanotubes 23 to the support portion 11 and is configured to allow the perspiration from the user to be absorbed by the carbon nanotubes 23 via the protective layer 24. In at least one embodiment, the protective layer 24 includes a non-woven fabric 240 located on the carbon nanotubes 23 and a wear resistant layer 241 located on the non-woven fabric 240 with micropores (not shown). The wear resistant layer 241 is made of glass or polymethyl methacrylate (PMMA). In another embodiment, the protective layer 24 is a ceramic layer with micropores.

When no perspiration is absorbed from the user by the detecting surface 230, the two electrode arrays 21 are electrically disconnected from each other since the carbon nanotubes 23 electrically connected to the two electrode arrays 21 are spaced from each other. When perspiration from the user is absorbed by the detecting surface 230, the perspiration can be adhered among the carbon nanotubes 23 and cause the carbon nanotubes 23 to become electrically connected to each other. Then, the two electrode arrays 21 are electrically connected to each other, thereby causing a resistance value of the electrode assembly 20 (which is equal to a resistance value between two second electrodes 222 of the electrode assembly 20) to decrease. When the amount of the perspiration absorbed by the detecting surface 230 increases, the resistance value of the electrode assembly 20 is decreased. When the carbon nanotubes 23 have absorbed a predetermined amount of perspiration from the user, the resistance value of the electrode assembly 20 reaches a minimum resistance value.

Figure 5:
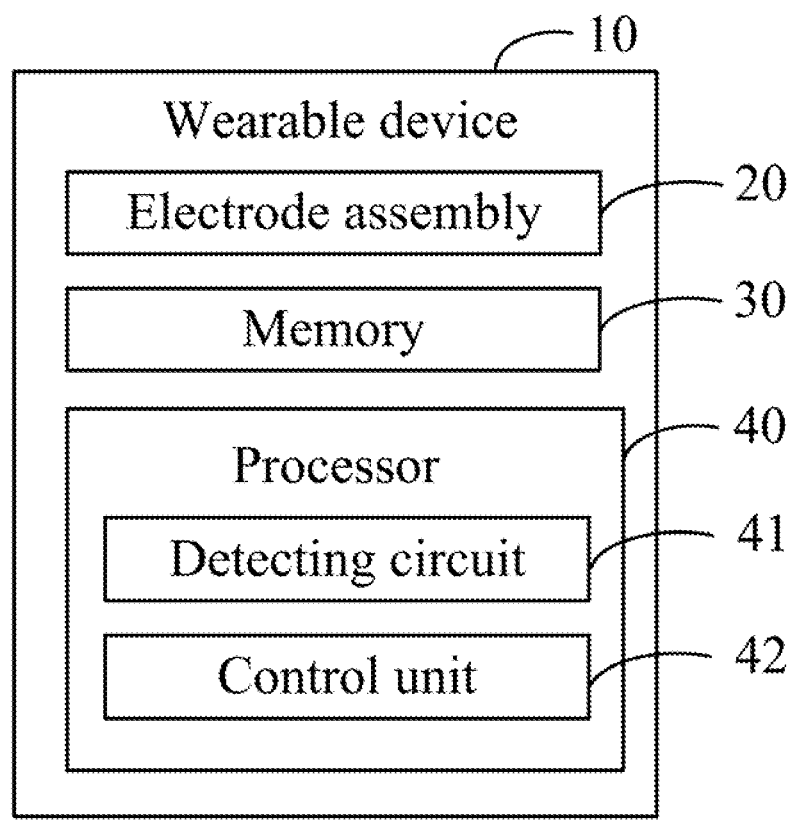
FIG. 5 is a block diagram of the wearable device of FIG. 1.

FIG. 5 illustrates that the wearable device 1 further includes a memory 30 and a processor 40. The memory 30 stores a relationship between different resistance values of the electrode assembly 20 and amounts of the perspiration. Each amount of the perspiration corresponds to one resistance value of the electrode assembly 20. The processor 40 detects a resistance value of each electrode assembly 20. The processor 40 further determines the amount of the perspiration corresponding to the detected resistance value according to the stored relationship. In at least one embodiment, the processor 40 further calculates a speed of the perspiration according to the determined amount of perspiration.

Figure 6:
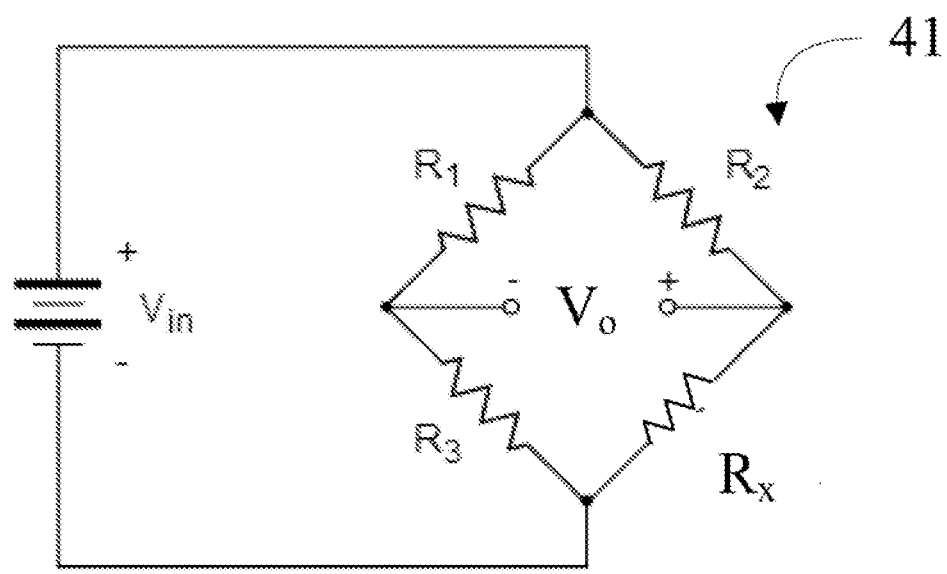
FIG. 6 is a diagrammatic view of a detecting circuit included in the wearable device of FIG. 5.

In at least one embodiment, the processor 40 includes at least one detecting circuit 41 and a control unit 42. FIG. 6 illustrates that each detecting circuit 41 is a Wheatstone Bridge which includes a resistor $R_1$, a resistor $R_2$, a resistor $R_3$, a voltmeter 410, and a DC power source 411. Two second electrodes 222 of each electrode assembly 20 are connected to the detecting circuit 41. The resistor $R_1$ and the resistor $R_3$ are connected to each other in series to form a first branch. The electrode assembly 20 and the resistor $R_2$ are connected to each other in series to form a second branch. The first branch and the second branch are connected to each other in parallel, and the connected first and the second branches are connected between an input terminal and an output terminal of the DC power source 411. Two ends of the voltmeter 410 are connected between the resistor $R_1$ and the resistor $R_3$ and between the electrode assembly 20 and the resistor $R_2$. The control unit 42 is electrically connected to the voltmeter 410 to obtain a reading $V_0$ of the voltmeter 410. As such, the control unit 42 can calculate the resistance value $R_x$ of the electrode assembly 20 according to the resistance values of the resistor $R_1$, the resistor $R_2$, and the resistor $R_3$, the reading $V_0$ of the voltmeter 410, and the output voltage $V_{in}$ of the DC power source, which is described as a function $R_x$ ($R_1$, $R_2$, $R_3$, $V_0$, $V_{in}$):

$$R_x = R_2 \frac{V_{in}R_3 + V_0(R_1 + R_3)}{V_{in}R_1 - V_0(R_1 + R_3)}$$

In another embodiment, the detecting circuit 41 is an ohmmeter which can determine the resistance value of the electrode assembly 20. Then, the control unit 42 can directly obtain the resistance value of the electrode assembly 20 from the ohmmeter.

In at least one embodiment, more than two electrode assemblies 20 are located on and secured to the support portion 11, and the electrode assemblies 20 have detecting surfaces 230 of different area sizes. Thus, time periods for the electrode assemblies 20 to reach the minimum resistance value of absorbing perspiration are different from each other. The greater area size of the detecting surface 230, the longer the time period for the electrode assembly 20 to reach the minimum resistance value. In this embodiment, the processor 40 further includes a number of detecting circuits 41 each electrically connected to one electrode assembly 20. Then, the processor 40 can detect the resistance value of each electrode assembly 20.

Each electrode assembly 20 is assigned a priority, which can be stored in the memory 30. The priority assigned to one electrode assembly 20 indicates an order for using the electrode assembly 20 to determine the amount of the perspiration when a previous electrode assembly 20 reaches the minimum resistance value. The less the area size of the detecting surface 230, the higher the priority is assigned to the electrode assembly 20. The electrode assembly 20 with a highest priority can reach the minimum resistance value within a minimum time period.

When the processor 40 determines that one electrode assembly 20 with a higher priority reaches the minimum resistance value (for example, when the reading of the voltmeter 410 of the detecting circuit 41 electrically connected to the electrode assembly 20 remains constant within a preset time period), the processor 40 subsequently detects the resistance value of a next electrode assembly 20 with a lower priority, and determines the amount of the perspiration from the user corresponding to the detected resistance value according to the stored relationship. As such, the processor 40 can continuously use different electrode assemblies 20 to monitor the perspiration from the user, until the electrode assembly 20 with the lowest priority reaches the minimum resistance value.

Furthermore, when the processor 40 detects the resistance value of the next electrode assembly 20, the processor 40 further controls the electrode assemblies 20 which have already reached the minimum resistance value to heat (for example, to energize the carbon nanotubes 23 of the electrode assemblies 20), thereby causing the perspiration adhered to the carbon nanotubes 23 to evaporate. As such, when the electrode assembly 20 with the lowest priority reaches the minimum resistance value, the processor 40 can subsequently use the electrode assemblies 20 with a higher priority to determine the perspiration again.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. A wearable device configured to monitor perspiration from a user, the wearable device comprising:
   a main body able to be worn by the user;
   a support portion protruding from an interior surface of the main body facing the user;
   at least one electrode assembly secured to the support portion, each of the at least one electrode assembly including two electrode arrays and a plurality of carbon nanotubes arranged in arrays, each electrode array including a plurality of arranged electrodes electrically connected to each other, the plurality of electrodes of each electrode array including at least two first electrodes each electrically connected to one of the plurality of carbon nanotubes, the plurality of carbon nanotubes electrically connected to the two electrode arrays being alternatively arranged on the support portion and spaced from each other to form a detecting surface, the plurality of carbon nanotubes configured to be electrically connected to each other when perspiration from the user is absorbed by the detecting surface, thereby causing a resistance value of the electrode assembly to decrease;

a memory for storing a relationship between different resistance values of the electrode assembly and amounts of the perspiration, each amount of the perspiration corresponding to one resistance value of the electrode assembly; and a processor configured to detect a resistance value of each of the at least one electrode assembly and determine an amount of the perspiration corresponding to the detected resistance value according to the stored relationship.

2. The wearable device of claim 1, wherein the two electrode arrays of each of the at least one electrode assembly face each other and are spaced from each other; the plurality of carbon nanotubes are located between the two electrode arrays; an extension direction of each of the plurality of electrodes of the two electrode arrays is parallel to a radial direction of the plurality of carbon nanotubes.

3. The wearable device of claim 1, wherein the two electrode arrays of each of the at least one electrode assembly face each other and are spaced from each other; the plurality of carbon nanotubes are located between the two electrode arrays; an extension direction of each of the plurality of electrodes of the two electrode arrays is perpendicular to an axial direction of the plurality of carbon nanotubes.

4. The wearable device of claim 1, wherein the plurality of electrodes of each electrode array further comprise a second electrode electrically disconnected from each of plurality of carbon nanotube; the resistance value of each of the at least one electrode assembly is equal to a resistance value between two second electrodes of the electrode assembly.

5. The wearable device of claim 4, wherein the processor comprises at least one detecting circuit and a control unit; each detecting circuit is a Wheatstone Bridge which includes a resistor $R_1$, a resistor $R_2$, a resistor $R_3$, a voltmeter, and a DC power source; the two second electrodes of each of the at least one electrode assembly are connected to the detecting circuit; the resistor $R_1$ and the resistor $R_3$ are connected to each other in series to form a first branch; the electrode assembly and the resistor $R_2$ are connected to each other in series to form a second branch; the first branch and the second branch are connected to each other in parallel, and the connected first and the second branches are connected between an input terminal and an output terminal of the DC power source; two ends of the voltmeter are connected between the resistor $R_1$ and the resistor $R_3$ and between the electrode assembly and the resistor $R_2$; the control unit is configured to obtain a reading $V_O$ of the voltmeter, and calculate the resistance value of the electrode assembly according to the resistance values of the resistor $R_1$, the resistor $R_2$, and the resistor $R_3$, the reading $V_O$ of the voltmeter, and the output voltage $V_{in}$ of the DC power source.

6. The wearable device of claim 5, wherein more than two electrode assemblies are located on and secured to the support portion; the electrode assemblies have detecting surfaces of different area sizes; the less the area size of the detecting surface, the higher a priority is assigned to the electrode assembly; the processor comprises a plurality of detecting circuits each electrically connected to one of the at least one electrode assembly; when the processor determines that one electrode assembly with a higher priority reaches a minimum resistance value, the processor is configured to subsequently detect the resistance value of a next electrode assembly with a lower priority, and determine the amount of the perspiration corresponding to the detected resistance value according to the stored relationship.

7. The wearable device of claim 6, wherein the processor is further configured to control the electrode assemblies which have already reached the minimum resistance value to heat, thereby causing the perspiration adhered to the plurality of carbon nanotubes to evaporate, and is configured to subsequently use the electrode assemblies with a higher priority to determine the perspiration again when the electrode assembly with the lowest priority reaches the minimum resistance value.

8. The wearable device of claim 4, wherein the processor comprises at least one detecting circuit and a control unit; the two second electrodes of each of the at least one electrode assembly are connected to the detecting circuit; the detecting circuit is an ohmmeter configured to determine the resistance value of the electrode assembly; the control unit is configured to directly obtain the resistance value of the electrode assembly from the ohmmeter.

9. The wearable device of claim 1, wherein the main body is a wristband.

10. The wearable device of claim 1, wherein the support portion is made of glass or plastic.

11. The wearable device of claim 1, wherein a protective layer is covered on the detecting surface, and is configured to secure the plurality of carbon nanotubes to the support portion, and allow the perspiration from the user to be absorbed by the plurality of carbon nanotubes via the protective layer.

12. The wearable device of claim 11, wherein the protective layer comprises a non-woven fabric located on the plurality of carbon nanotubes and a wear resistant layer located on the non-woven fabric and with micropores.

13. The wearable device of claim 12, wherein the wear resistant layer is made of glass or polymethyl methacrylate.

14. The wearable device of claim 11, wherein the protective layer is a ceramic layer with micropores.

15. The wearable device of claim 1, wherein the processor is further configured to calculate a velocity of the perspiration according to the determined amount of perspiration.

* * * * *